United States Patent [19]
Glassman

[11] Patent Number: 5,209,243
[45] Date of Patent: May 11, 1993

[54] CESARIAN SECTION COLLECTING INCISE DRAPE

[76] Inventor: Jacob A. Glassman, 1680 Michigan Ave., Miami Beach, Fla. 33139

[21] Appl. No.: 778,663

[22] Filed: Oct. 18, 1991

[51] Int. Cl.$^5$ .................... A61B 19/00; A61B 19/08
[52] U.S. Cl. .................................. 128/849; 128/853
[58] Field of Search ........................... 128/849–856

[56] References Cited

U.S. PATENT DOCUMENTS

| | | | |
|---|---|---|---|
| 3,244,169 | 4/1966 | Baxter | 128/850 |
| 3,538,912 | 11/1970 | Becker | 128/853 |
| 3,650,267 | 3/1972 | Anderson | 128/853 |
| 3,668,050 | 6/1972 | Donnelly | 128/849 |
| 3,695,260 | 10/1972 | Endres | 128/853 |
| 3,763,857 | 10/1973 | Schrading | 128/853 |
| 4,489,720 | 12/1984 | Morris | 128/853 |
| 4,559,937 | 12/1985 | Vinson | 128/853 |
| 4,596,245 | 6/1986 | Morris | 128/853 |
| 4,974,604 | 12/1990 | Morris | 128/855 |
| 5,002,069 | 3/1991 | Thompson | 128/853 |

*Primary Examiner*—Robert A. Hafer
*Assistant Examiner*—Michael Brown

[57] ABSTRACT

A Cesarian Section Collecting Incise Drape, for collecting and retaining out-gushing amniotic fluid that escapes from an opened amniotic sac during surgery. Specifically, the drape comprises a waterproof main body drape having an incise opening that overlies and exposes a wide operative area on the body covered thereby. In order to collect such fluid a sheet of clear transparent plastic material or its equivalent, having an opening therein of larger size than the bottom incise opening of the main body drape, whereupon its external peripheral margins are secured to the main body drape by adhesive means, such as adhesive tape, heat-seal, or cement to form a waterproof bag that will receive waste fluids rapidly flowing therein.

Furthermore, the results obtained by the aforementioned constructed drape collecting bag combination may also be achieved by the use of a clear transparent plastic sheet like that described hereinabove, and subsequently affix it by a waterproof adhesive or heat-seal around its outer edges onto any brand of a regular body drape that has a traditional operative opening and thus avoid the need and extra cost of obtaining a ready factory made C-Section Collecting Drape.

7 Claims, 2 Drawing Sheets

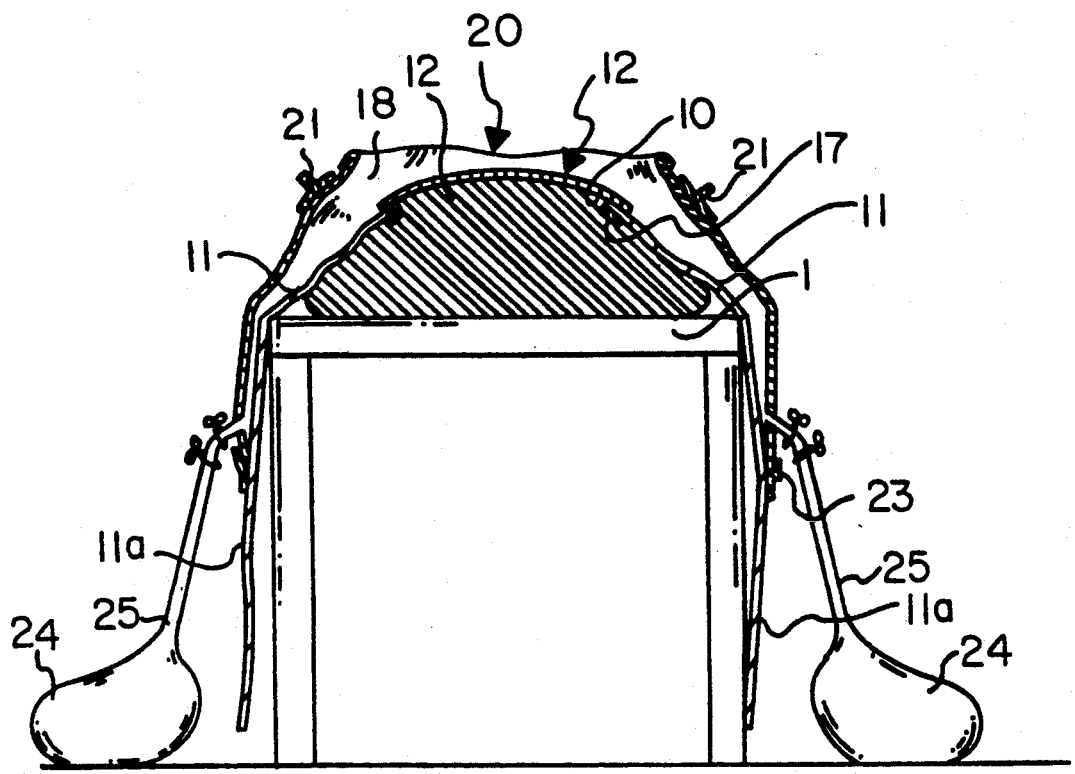
FIG. 3
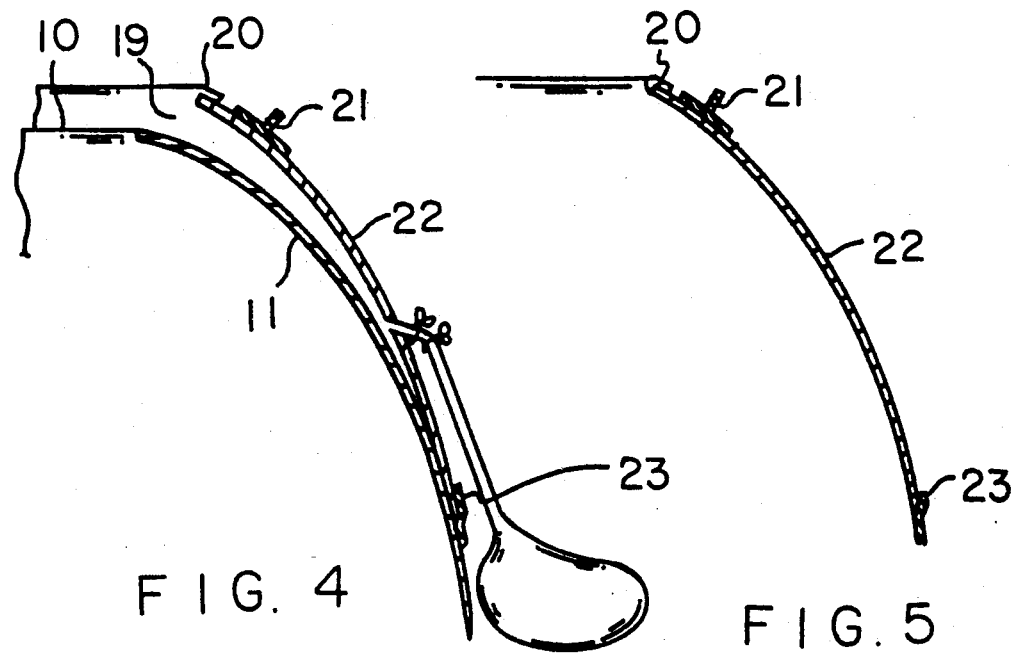
FIG. 4
FIG. 5

CESARIAN SECTION COLLECTING INCISE DRAPE

CROSS REFERENCE TO RELATED APPLICATIONS

This application is related to Ser. No. 314,081 filed Feb. 23, 1989, now abandoned.

The invention relates to a Cesarian Section Collecting Incise Drape with a built-in collecting means to trap the outgushing of amniotic fluid as it suddenly escapes from the opened amniotic sac when once it is incised. Until now the amniotic fluid was allowed to pour out and spill all over the drapes, surgeon's gown, and operating room floor. Today this is a most serious accident because AIDS is spreading at an alarming rate and every precaution must be taken to prevent being contaminated by the virus-containing amniotic fluid from the mother with AIDS. When the amniotic fluid suddenly escapes from the uterus it spreads out in all directions. But more especially, it spreads out laterally on both sides, and inferiorly down to the groin. The only way to capture or entrap this escaping fluid is to provide a collecting system that will entrap the fluid at any point in its 360 degree circular opening. Unless the operating table is tilted so that the head is lowered (a position referred to as a Trendelenburg position), the flow of the amniotic fluid is rarely upwards.

The Cesarian Section Collecting Incise Drape described herein offers several advantages to the surgeon, the patient, and operating room personnel. The patient benefits from the incise drape because it helps to prevent bacterial infection throughout the surgical procedure. The sterile incise drape by virtue of its adhesive strips around the edges of the fenestration, both on top and bottom, keeps the main body drape fixed to the skin surface of the abdomen. More importantly, the plastic incise drape is carefully laid down over the skin of the abdomen AND literally blocks all the openings or outlets of the sweat with its sudoriferous and sebaceous glands within the skin. In so doing, the plastic incise drape blocks off a variety of bacteria that are constantly present in the sebaceous and sudoriferous glands and thereby prevents them from spreading toward the site of the operative wound. The oil and sweat are constantly contaminated with staphylococci epidermidis and aureus, and other low grade bacteria. It is these organisms that are responsible for postoperative wound infections. Today there is such great concern regarding AIDS that every possible precaution must be taken to prevent contamination by the AIDS virus; this includes the surgeon, assistant, nurses, and operating room personnel. As a result they carefully stand clear of any of the patient's bodily secretions, such as amniotic fluid, serum, blood, pus or any form of drainage material. All personnel in the operating room with open sores or fresh cuts or injuries, are most careful not to come into direct contact with any of these fluids, especially when the mother is reported to have AIDS or is suspected of it. The purpose of the collecting pouch described herein, is to reduce the present-day fear that attends the surgery of a cesarian section. Potentially infected amniotic fluid is so readily trapped and kept trapped in the pouch, to be drained off by a side communicating container, that the attending fears of the operating room personnel have been greatly allayed. The built-in fluid collection features should instill a feeling of safety and confidence among those surgeons, nurses, and O.R. attendants who have to deal with the surgery of a cesarian section (C-Section) and postoperative clean-up of the operating room wastes.

This new Cesarian Incise Collection Drape is constructed of a lesser number of parts, and unimportant trimmings than in the present-day C-Section drape. Most important is the new feature of 360 degree fluid collection offside drainage feature, which may be applied to any present-day ordinary surgical drape.

The C-Section drape in use today is too expensive, too bulky, too many parts, too shallow, and has an excess of unnecessary trimmings. Also, it has no run-off site for the final removable collection of fluids. For example, the C-Section drape of today is constructed by permanently attaching a large, completely formed transparent plastic bag to the main body drape. This complete plastic bag is sealed to the bottom drape at its peripheral edges with adhesive tape, cement, glue or by heat-sealing. The bag has two openings or fenestrations; one larger opening on top and one smaller opening at the bottom. The bottom opening of the plastic bag is glued permanently to the topside of the main body drape, so that the two openings are properly aligned, and a common opening or fenestration is established. The larger opening on the topside of the plastic bag, allows the surgeon to operate through it with ease. The edges of the topside opening are trimmed with a stiffening border material to help maintain the patency between the top and bottom layers; this prevents the top layer from collapsing onto the bottom layer of the bag and thus obliterating the provided space.

The underside around the opening of the main body drape has a wide area of adhesive material, that is kept covered by a non-adhesive protective layer; the protective layer is removed before the adhesive layer can be applied to the skin surface of the abdomen. After the amniotic sac is opened, the amniotic fluid rushes into the 360 degree opening of the topside plastic bag and settles to the sides and bottom of the plastic bag. Present C-Section bags do not have safety bottom drainage bags to drain away the contaminated fluid, to be finally sealed and disposed of without personal contact.

Accordingly, it is the object of the invention to provide a Cesarian Section Incise Collecting Drape with a built-in collection bag that will catch or trap all the fluids escaping from an opened amniotic sac, and allow the fluids to gravitate or drain to a lower level at the sides of the patient's table where a final collection and no-contact disposal of contaminated fluid is carried out.

Another object is to provide an incise drape that will help in preventing viral contamination, and bacterial infection during and, more importantly, after the surgical procedure.

Another object is to incorporate in a body drape with an adhesive means to retain the body drape in a desired position by adhesively securing it to the selected site on the body surface.

Another object is to create a bag device made of waterproof material, such as transparent plastic, or non-woven material that will have a communication with the surgical opening in the main body drape that will receive, trap and contain the outgushing fluids such as amniotic fluid, ascitic fluid and escaping bile or serum; and ultimately permit the fluids to gravitate to a lower level at the sides of the patient's O.R. table.

Another object is to provide an abdominal drape having a surgical opening with an attached means fitted to said opening to collect and retain contaminated fluids to prevent a spill-over of contaminated fluids onto the operating personnel and floor of the operating room, and a final dependent collecting bag that can be aseptically sealed and disposed of.

Another object is to provide a surgical abdominal incise drape with a collection means creating a bag surrounding and communicating with the surgical opening that includes a stiffening means at the edge or below the edge of the topside opening to help maintain the patency of the bag while entrapping the escaping fluids. These stiffening means may be metallic strips adhesed to the plastic either in transverse or vertical positions.

The structure by means of which the above noted and other advantages of the invention are attained will be described in the following specification, taken in conjunction with the accompanying drawings, showing the preferred illustrative embodiments of the invention in which:

FIG. 3 is a sectional view of the work table and patient covered by the cesarian drape, illustrating the very low level of the fluid collection bag relative to the patient and the lowest, bi-lateral collecting or drainage bags that may rest on the floor (24 and 25), and which are clamped off--and sealed for safe disposal of contaminated waste.

FIG. 4 is a vertical sectional view of the fluid receiving bag which completely surrounds the surgical area.

FIG. 5 is a vertical sectional view of the plastic sheet, the bag which is shown to illustrate its use apart from a complete bag and which may be told from the complete bag illustrated in FIG. 4. Also included, is the final gravity drain-off collecting bag.

DESCRIPTION OF INVENTION

Figure 1:
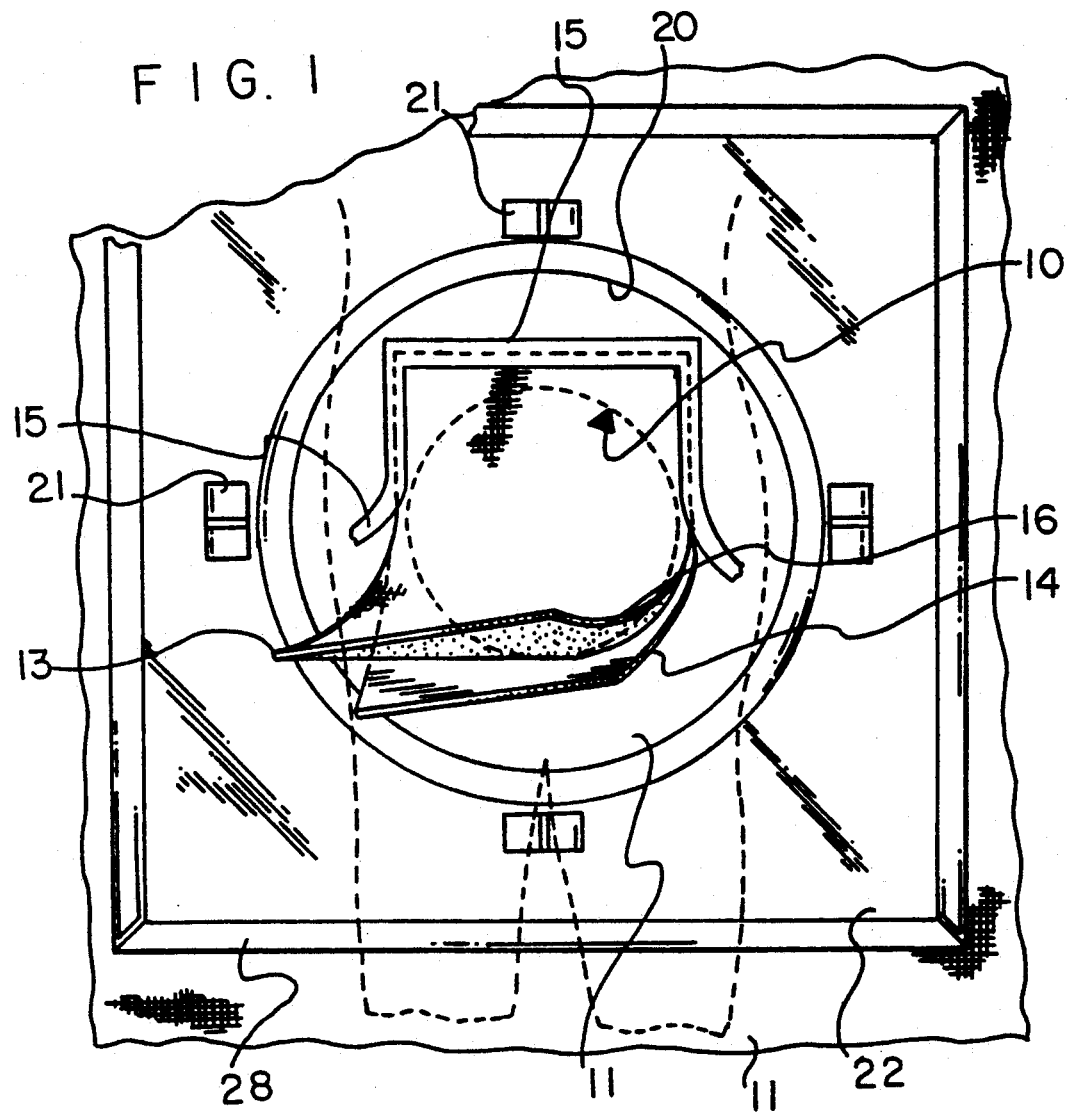
FIG. 1 is a top plan view of the Cesarian Section Drape, showing the bag to receive waste fluids affixed to the body drape, and with the bag opening overlying the surgical area.
Figure 2:
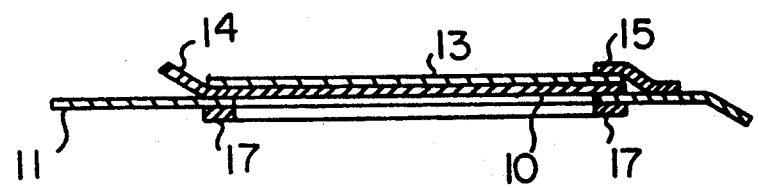
FIG. 2 is a detail section of the fenestration in the drape, prior to removal of the adhesive coated incise drape and its main adhesive cover.

The invention, best illustrated in FIG. 1, provides improvements over the structure and function of a sterile Cesarian Section Incise Collecting Drape, that has a surgical cut-out (10) centrally located on a waterproof main body drape (11) of sufficient size to completely cover the pregnant patient, with the cut-out (10) overlying the selected abdominal area (12). The cut-out area (10) has a two layered incise flap (13-14) normally closing opening (10). When the main body drape is in place over the abdomen, it is adjusted to the precise site of the projected surgical opening (10). The flaps (13-14), which are held in place by a fixed adhesive strip (15), are first elevated as illustrated in FIG. 1. By peeling strip (14) off the adhesive surface (16) on flap (13) and removing it, the adhesive surface of flap (13) is then carefully laid down over the abdominal skin surface of the selected precise operative area. The flap (13) being an adhesive layer fixes the abdominal skin to the main body drape. The adhesive incise drape overlaps the edges of the fenestration, thus completely sealing off the surgical wound. The plastic adhesive layer need not be confused with a flap; it may be permanently attached to the opening of the main drape on all sides. The sheet (11) covering the body, has an adhesive (17) on its underside immediately surrounding the edges of the fenestration or cut-out (10). This enables the body sheet or drape (11) to be adhesively secured to the body. This seals the main body drape to the abdomen while at the same time waterproofs the junction between body drape and topside collecting bag.

Referring now to FIG. 3, which is illustrative of the application of the body drape (11) over the body (12). It should be noted that the body is placed on table (1) that is relatively narrow in width to allow the side portions (11a) of the bag (18) to open upwardly, outwardly, and especially downwardly, so as to cause the newly created fluid collecting means comprising bag (18) to remain open and functional, as at (19) in FIG. 4. The presence of malleable, long flexible T-shaped metal stiffeners (21) glued to the plastic wall (22) maintain the bag open thus reducing the chances of the walls from collapsing. Any preferred flexible means transverse or longitudinal means to accomplish separation of the top and bottom bag layers may be employed - even a metallic or plastic fuzzy strip adhesed to the very edge of the topside opening is workable.

The large fenestration (20) in the topside layer (22) of the bag (18) permits the surgeon to operate through the bottom smaller fenestration (10) in the main body drape (11).

The advantages of the newly constructed C-Section drape are:

1. Simpler construction requiring less parts and therefore less material, and less cost of construction; also, it permits greater dependent side portions to the bag, with final dependent fluid collection for final and safe disposal to safeguard all operating-room personnel.

2. Unessential trimmings are eliminated. A simpler and more effective means to maintain the separation and patency between the top and bottom layers of the collecting bag, are the thin glued-on long transverse, longitudinal, or T-shaped-malleable-metallic stiffeners (21) spaced around and below the edges of the top of the fenestration:

3. Simpler application of the adhesive means, as well as an exact positioning over the precise operative site.

Where other drapes attach to the abdominal surface by virtue of special adhesive coatings applied around the undersurface of the main body drape, this new drape employs isotope adhesive strips (17) that are glued close to the very edges of the underside of the fenestration (10) of the main body drape. Before applying this body drape to the abdomen the proper strips are first removed.

Essentially, the applicant's C-Section Incise Drape, completely eliminates the need of a complete, preformed plastic bag permanently cemented to the topside of a regular body drape to trap outpouring amniotic fluid. The applicant instead creates the same collecting bag with only one topside plastic layer (22) of a required size by heat-sealing, gluing, or cementing it directly to the topside of the waterproof non-woven main body drape (11). Securing the edges of the topside layer (22) to the bottom-side layer (11) may be sealed by adhesive tape (23), glue, cement, or heat-sealing. By employing the Glassman-Kimberly-Clark Universal Incise Drape as the bottom body drape (11), a great savings is made, because that drape is particularly suitable to the construction of the new C-Section drape.

As to the advantages offered by the applicant's drape, they are: The drape (11) may be moved around until the ideal operative site is found, and then it is fixed finally to the abdominal wall of the body by bottom-side iso-seal adhesive strips. If the drape fenestration (10) is found not to be ideally placed, the surgeon need only lift up the adhesive strips and rearrange the fenestration of the drape once again. When the desired operative site is selected, the adhesive incise flap (13) is laid down irrevocably onto the abdominal skin surface.

Applicant's C-Section drape can also be made up as a Mini-C-Section collecting drape, by using the same unique bag structure as described above, and use only the top-side-section, thus eliminating the entire bag structure. This reduced-in-size mini-drape may be used over any ordinary surgical drape that provides an adequate operative fenestration. The top-side-mini-C-Section drape is merely superimposed, and fixed by its peripheral adhesive undersurface to the bottom main body regular drape. The newly converted C-Section drape will be able to effectively collect the sudden rush of fluids, amniotic or ascitic, and finally store it bi-laterally to be clamped-off and safely disposed of.

Now the newly improved C-Section drape can function as a fluid collection bag (18) and effectively collect outpouring fluids of amniotic fluid, ascitic fluid from cirrhotic patients, bile from leaking biliary ducts, and finally blood from hemorrhaging blood vessels such as the aorta and iliac arteries. There also will be instances of AIDS consideration where the surgeon will demand final fluid drainage by the collecting bags (24) and (25) to trap large amounts of irrigating fluids drain such as when irrigating large AIDS' infected wounds. Trapping and sealing AIDS contaminated fluids by bags (24) and (25) assure the O.R. personnel of no contact with the infected fluids.

The topside may employ a fenestration of any size and shape (round, oval, oblong, etc.), so long as the topside fenestration (20) remains appreciably larger than the main body drape opening below.

Many details may be varied without departing from the spirit of the invention. Therefore, the scope of the claims is not limited except by their terms:

What I claim and desire to secure by Letters Patent of the United States is:

1. A cesarian section incise collecting drape adapted to be draped over the body of a patient lying on an operating table, said patient's body having an upper surface and downwardly extending side surfaces, comprising a bottom layer of impervious flexible material having a first opening therethrough a top layer of impervious flexible material having a second opening therethrough, said second opening being larger than said first opening, said first opening being located within the confines of said second opening, said top layer being sealingly connected to said bottom layer around an outside edge of said top layer forming impervious collecting means extending substantially around said first and second openings for collecting body fluids produced during a cesarian section surgical operation said collecting means comprising a space formed between said first and second layers extending around said first and second openings thereby creating a collecting chamber between said top and bottom layers of impervious flexible material whereby at least some portion of said collecting chamber extends downwardly along a portion of said side surface of the body of said patient.

2. The cesarian section incise collecting drape of claim 1 including stiffening means associated with said bag means for spacing the second opening in said top layer away from said bottom layer.

3. The apparatus of claim 1, wherein said leak proof seal is formed by heat-sealing together said top and bottom layers of impervious flexible material.

4. The apparatus of claim 1, wherein said leak proof seal is formed by adhesively bonding together said top and bottom layers of impervious flexible material.

5. The apparatus of claim 1, including a removable layer of material overlying said first and second openings in said top and bottom layers of material.

6. The apparatus of claim 1, wherein said leak proof seal between said top and bottom layers of impervious flexible material is spaced away from the periphery of said second opening by a distance which allows said collecting chamber to extend downwardly when the drape is placed over the body of a person to be operated upon in such a manner as to cause escaping fluids from the body to flow downward into said collecting chamber.

7. The apparatus of claim 6 including a collecting container in flow communication with said collecting chamber and means for shutting off flow communication of said collecting chamber with said collecting container.

* * * * *